US009291725B2

(12) United States Patent
Wang et al.

(10) Patent No.: US 9,291,725 B2
(45) Date of Patent: Mar. 22, 2016

(54) RANDOM COINCIDENCE REDUCTION IN POSITRON EMISSION TOMOGRAPHY USING TANGENTIAL TIME-OF-FLIGHT MASK

(75) Inventors: Wenli Wang, Briarcliff Manor, NY (US); Xiaofeng Niu, Mundelein, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 909 days.

(21) Appl. No.: 13/472,533

(22) Filed: May 16, 2012

(65) Prior Publication Data

US 2013/0311142 A1    Nov. 21, 2013

(51) Int. Cl.
*G01T 1/29* (2006.01)
*A61B 6/03* (2006.01)

(52) U.S. Cl.
CPC .............. *G01T 1/2985* (2013.01); *A61B 6/037* (2013.01)

(58) Field of Classification Search
CPC ......... G01T 1/2985; G01T 1/172; G01T 1/17; G01T 1/1611; G01T 1/2914; A61B 6/037; A61B 6/03
See application file for complete search history.

(56) References Cited

U.S. PATENT DOCUMENTS

| 6,294,788 | B1 * | 9/2001 | Cooke et al. ............. 250/363.03 |
| 7,737,405 | B2 | 6/2010 | Watson et al. |
| 2007/0106154 | A1 * | 5/2007 | Conti .................... G01T 1/1611 600/436 |
| 2008/0284428 | A1 * | 11/2008 | Fiedler et al. ................ 324/307 |
| 2008/0296505 | A1 | 12/2008 | Cooke et al. |
| 2008/0317194 | A1 | 12/2008 | Gagnon et al. |

FOREIGN PATENT DOCUMENTS

| JP | 2001-356172 A | 12/2001 |
| JP | 2009-519437 A | 5/2009 |
| JP | 2009-522582 A | 6/2009 |

OTHER PUBLICATIONS

Maurizio Conti "Tailoring PET Time Coincidence Window Using CT Morphological Infromatioin", 2006 IEEE Nuclear Science Symposium Conference Record, p. 2349-2353.
Jonathan K Poon, et al., Optimal whole-body Pet scanner configurations for different volums of LSO scintillator: a simulatiion study, submitted to physics in Medicine and Biology, 2012, Number of pp. (19).
International Search Report and Written Opinion of the International Searching Authority Issued Jun. 11, 2013 in PCT/JP2010/063626 (with English translation of Categories of Documents).

(Continued)

*Primary Examiner* — Manuel L Barbee
(74) *Attorney, Agent, or Firm* — Oblon, McClelland, Maier & Neustadt, L.L.P.

(57) ABSTRACT

A method and apparatus for reducing random events in positron emission tomography (PET) list mode data, the method including the steps of obtaining, for a PET scanner having a given reconstruction field of view (FOV), time-of-flight (TOF) prompt list-mode count data that includes TOF information, the TOF prompt list-mode count data including a plurality of entries; and filtering the obtained prompt list-mode count data by removing those entries in the obtained prompt list-mode count data that represent emission points lying outside a tangential TOF mask to obtain filtered list-mode count data.

12 Claims, 5 Drawing Sheets

(56) References Cited

OTHER PUBLICATIONS

Office Action mailed on Dec. 22, 2015 for Chinese Application No. 201380000774.8.

Maurizio Conti et al.; "Tailoring PET Time Coincidence Window Using CT Morphological Information"; IEEE Transactions on Nulcear Science, vol. 54, No. 5, Oct. 2007, pp. 1599-1605.

* cited by examiner

RANDOM COINCIDENCE REDUCTION IN POSITRON EMISSION TOMOGRAPHY USING TANGENTIAL TIME-OF-FLIGHT MASK

FIELD

Embodiments described herein relate generally to random event filtering in time-of-flight data acquired in a gamma ray detection system.

BACKGROUND

Positron emission tomography (PET) is a branch of nuclear medicine in which a positron-emitting radiopharmaceutical is introduced into the body of a patient. As the radiopharmaceutical decays, positrons are generated. More specifically, each of a plurality of positrons reacts with an electron in what is known as a positron annihilation event, thereby generating a coincident pair of gamma photons which travel substantially in opposite directions along a line of coincidence. A gamma photon pair detected within a coincidence time is ordinarily recorded by the PET scanner as an annihilation event.

In time-of-flight ("TOF") imaging, the time within the coincidence interval at which each gamma photon in the coincident pair is detected is also measured. The time-of-flight information provides an indication of the annihilation location of the detected event along the line of coincidence. Data from a plurality of annihilation events is used to reconstruct or create images of the patient or object scanned, typically by using statistical (iterative) or analytical reconstruction algorithms.

Figure 1:
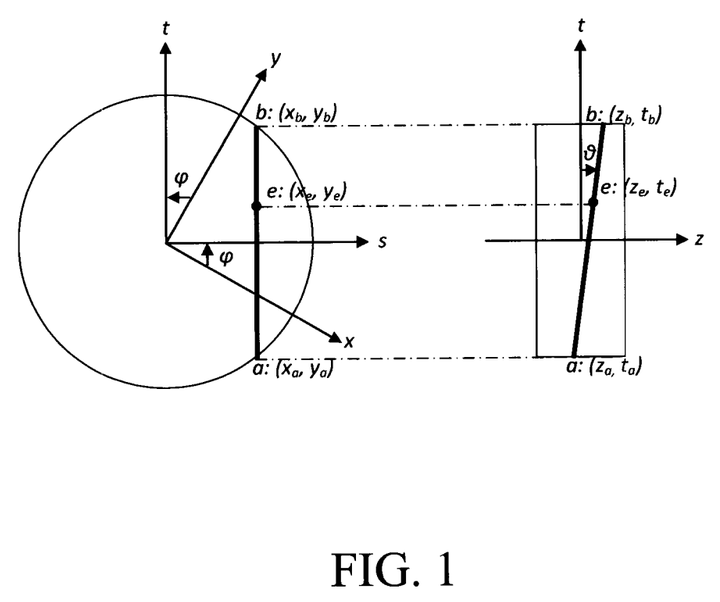
FIG. 1 illustrates an example of a geometry of a PET imaging apparatus.

FIG. 1 illustrates the transaxial and axial coordinates of an emitted positron and the measured line of response (LOR) of a 3D detector. The coordinates $(x_e, y_e, z_e)$ or $(s_e, t_e, z_e)$ define the emitted positron's image coordinate. The measured LOR's projection coordinate can be defined by either $(s, \phi, z, \theta)$, where $z=(z_a+z_b)/2$, or may include the additional dimension $t$ for a TOF-LOR.

In PET, random coincidences occur due to the finite width of the coincidence window, which is used to detect true coincidences. If two uncorrelated single events are detected within the coincidence window, they can mistakenly be identified as a true coincidence event and recorded. The rate of random events is proportional to the single event rate on each detector and the size of coincidence window, as shown in Equation (1):

$$C_{ij} = 2\tau r_i r_j \quad (1)$$

in which $C_{ij}$ represents the random coincidences count rate on the LOR that connects the i-th and j-th detectors, $r_i r_j$ represents the single count event rates of the i-th and j-th detectors, and $\tau$ is the coincidence window size.

Random coincidences can comprise a large portion of the recorded prompt coincidence events (which include true, scatter, and random coincidence events), especially in the operation of a 3D PET scanner and high radioactivity concentration. If not compensated for properly, random coincidence events can introduce substantial quantitative errors in the reconstructed images.

The amount of random events in prompt coincidence events is determined by the coincidence timing window and the single event count-rate of two opposing crystals that detect the coincidence. The coincidence timing window is set by the size of the acquisition field-of-view (FOV) and the timing resolution of the scanner. The typical FOV for a PET scanner is a three-dimensional cylinder, with a centered circular region in the transverse plane and the same axial length as the scanner. Therefore, by default, the acquisition FOV refers to the diameter of the circular region in the transverse plane. For PET whole-body imaging, the FOV is usually 576 mm to 700 mm. The timing resolution depends on the type of crystal, optical photon detector, and front-end electronics of the data acquisition system. For LYSO crystals, the typical timing resolution is 500 ps to 650 ps. The related coincidence timing window is then 4 ns to 6 ns for whole-body imaging. The random fraction (random/prompt) in FDG whole-body applications is about 30% to 50%, depending on the activity concentration of the axial section of the patient.

However, the fixed coincidence window method inevitably introduces a large amount of random events in the prompt coincidence data. For example, for a fixed phantom/patient with the same single event count-rate over all crystals, the total amount of randoms is directly proportional to the circular area of the acquisition FOV and the coincidence window FOV size. Note that the coincidence window FOV can be computed as 2*150 (mm 1 ns)*coinWin (ns), in which coinWin is the coincidence window length in ns.

Various methods have been proposed to reduce the number of random events.

In one approach, a truncated time window smaller than the maximum time coincidence window of the PET scanner is used to restrict projection data acquisition to only a central subset of TOF bins that is less than all available TOF bins. The truncated time-window FOV can represent a region of interest of an object being imaged that is smaller than the actual object. It can also lower the list-mode data transfer rate, e.g., for a high-count-rate Rb-82 PET cardiac imaging application. This truncated time window method not only reduces the number of random events, but also reduces the number of true events, if the truncated time window is set too aggressively.

In another approach, an individual patient's CT morphological information is used to tailor the time coincidence window. For a particular line-of-response (LOR), the lower- and upper-bound of the TOF bins are determined by finding the entrance and exit points of the LOR that intersects with the patient's body. The effect of the TOF masking is a trimming of the sinogram along the boundary of the patient, eliminating events outside the patient that are mainly random. However, since the statistical uncertainty of timing (i.e., the timing resolution is not perfect) is not taken into consideration, about 10-15% of true coincidences are also rejected in this TOF masking approach.

In a third approach, a variable coincidence window as a function of different ring differences is used to reduce random events. This method is more applicable for long axial-FOV PET scanners, e.g., those having greater than a 20-cm axial FOV.

Other random reduction methods include using an adjustable coincidence window between different pairs of detector modules, and/or using sinogram radial bin locations to reject LORs that are located outside the FOV. These methods do not take timing resolution into consideration, and thus will inevitable also reduce true coincidence events.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Embodiments disclosed herein are directed to a general-purpose random event reduction technique that only utilizes the TOF resolution and acquisition FOV information. The embodiments remove all random coincidences that do not contribute to the acquisition FOV, but they do not affect true coincidence events.

According to one embodiment, there is provided a method of reducing random events in positron emission tomography (PET) list mode data, the method comprising: (1) obtaining, for a PET scanner having a given reconstruction field of view (FOV), time-of-flight (TOF) prompt (or delay) list-mode count data that includes TOF information, the TOF prompt (or delay) list-mode count data including a plurality of entries; and (2) filtering the obtained prompt (or delay) list-mode count data by removing those entries in the obtained prompt (or delay) list-mode count data that represent emission points lying outside a tangential TOF mask to obtain filtered list-mode count data.

In one embodiment, the filtering step comprises removing each entry for which the following inequality, representing the tangential TOF mask, is not satisfied:

$$\frac{c}{2}|t_a - t_b|\cos\theta \le \sqrt{\frac{d^2}{4} - s^2} + n\sigma_{TOF}$$

wherein $t_a$ and $t_b$ are respective arrival times of events a and b included in the entry, c/2 is a conversion factor to convert time into distance (c is the speed of light), $\theta$ is an axial tilt angle with respect to the transverse plane of a line-of-response represented by the entry, d is a diameter of the reconstruction FOV, s is a radial distance value of the line-of-response represented by the entry, $\sigma_{TOF}$ is a standard deviation of the PET scanner timing resolution converted into a spatial domain, and n is a predetermined value, preferably in the range [2, 3] and indicates the confidence interval that a true LOR will not be removed by the mask.

Further, in one embodiment, the method further comprises performing reconstruction on the filtered list mode count data.

Turning now to the figures, the reconstruction FOV is usually set as a cylinder with a fixed diameter in the transverse plane and with an axial length covering the scanner's axial FOV. Thus, in the transverse plane, the circular FOV can be determined by a spatial 2D coordinate system, e.g., the radial "s" and tangential "t" projection coordinates, as shown in FIG. 1.

The spatial resolution is dramatically different in the projection's radial and tangential directions. The radial resolution is determined by scanner's transverse crystal size, whose FWHM is usually 2~4 mm (e.g., given a 4 mm crystal pitch). The tangential resolution is determined by the system timing resolution, whose FWHM, if transformed to the spatial domain, is 60~90 mm (e.g., given a 400~600 ps timing resolution).

Figure 2:
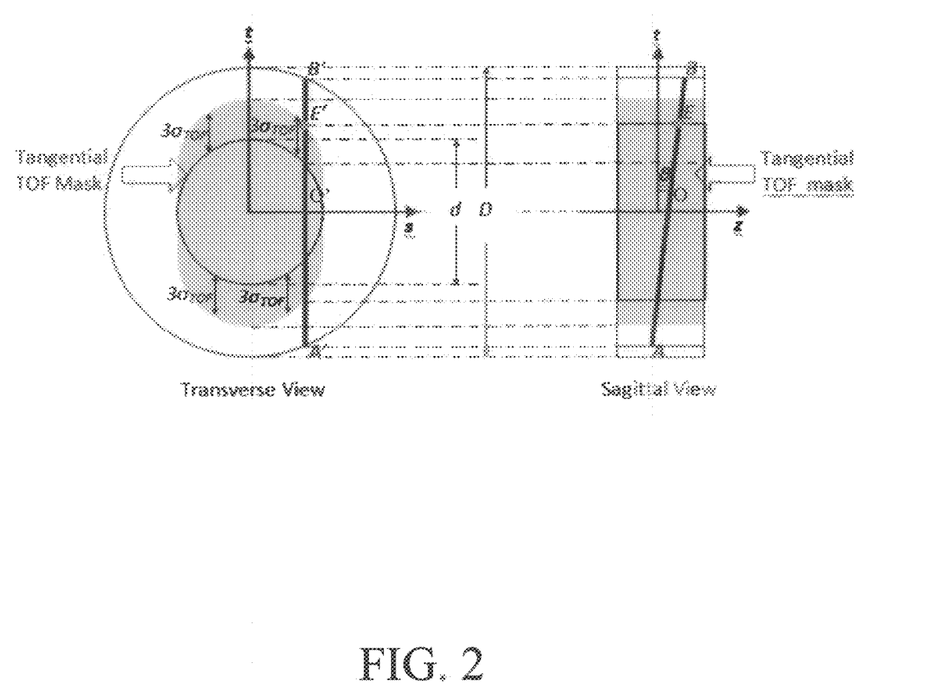
FIG. 2 illustrates a novel TOF mask for a circular cylinder in both transverse and sagittal views.

In one embodiment, a tangential TOF mask, illustrated as the shaded area in FIG. 2, is used to reduce the amount of random events and possible scatter in prompt data. In particular, when the following equation is satisfied, the true data for a given LOR b is maintained and not removed by the filter:

$$\frac{c}{2}|t_a - t_b|\cos\theta \le \sqrt{\frac{d^2}{4} - s^2} + n\sigma_{TOF} \qquad (2)$$

where $t_a$ and $t_b$ is the arrival time (in ps) of events a and b, respectively, c/2=0.15 mm/ps is the conversion factor to convert ps into mm, θ is the axial tilt angle of the line-of-response with respect to the transverse plane, d is the diameter of the reconstruction FOV, $\sigma_{TOF}$ is the standard deviation of the system timing resolution converted into the spatial domain, and n is a predetermined value that is preferably in the range of [2, 3]. The TOF mask is essentially stretching the reconstruction FOV cylinder along the ±t dimension by $n\sigma_{TOF}$. The term $$\sqrt{\frac{d^2}{4} - s^2}$$

is half of the chord length of line A'B' intersecting with the circle FOV with diameter d. The term $$\frac{c}{2}|t_a - t_b|$$

represents the distance of the emission point E to the middle point O of the LOR, i.e., segment OE.

Note that the emission point can be anywhere along the LOR AB. In FIG. 2, the emission point happens to be at the edge of the TOF mask. The term $$\frac{c}{2}|t_a - t_b|\cos\theta$$

is simply the projection of OE in the transverse plane.

For Gaussian distributed timing resolution, $3\sigma_{TOF}=3*FWHM_{TOF}/2.355$, and with 450 ps $FWHM_{TOF}$, $3\sigma_{TOF}=86$ mm. Note that $\pm 3\sigma_{TOF}$ is used to achieve a 99.7% confidence interval. If reducing the confidence interval to 95.4%, then only $\pm 2\sigma_{TOF}$ is needed and more random events and possible scatter events will be removed.

Assuming that the random distribution is uniform in the (s, t) dimensions, before using any TOF mask, the number of random events in (s, t) dimensions is proportional to d·2·150 (mm/ns)·coinWin (ns). After using the tangential TOF mask, the number of random events in (s, t) dimensions is proportional to $2n\sigma_{TOF}d+\pi d^2/4$.

It has been shown that the number of random events can be reduced by 50% for a given IEC phantom, which in turn increases the noise-equivalent-count rate by 12%, even without using TOF reconstruction.

Also, note that the TOF mask can also be used for other shape reconstruction FOVs, e.g., those more conformal to a patient's transverse cross-section.

Figure 3:
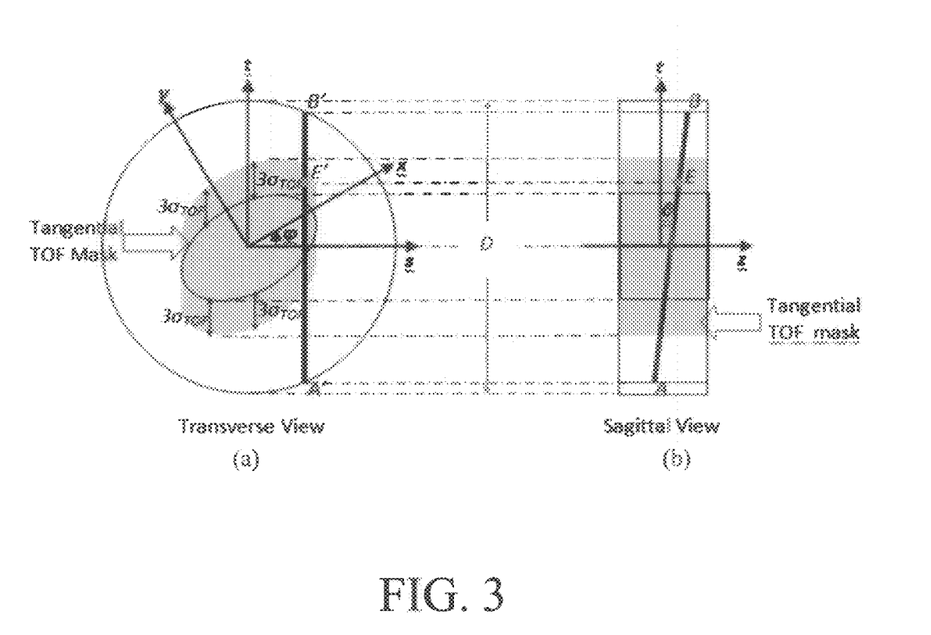
FIG. 3 illustrates a novel TOF mask for an elliptical cylinder in both transverse and sagittal views.
Figure 4:
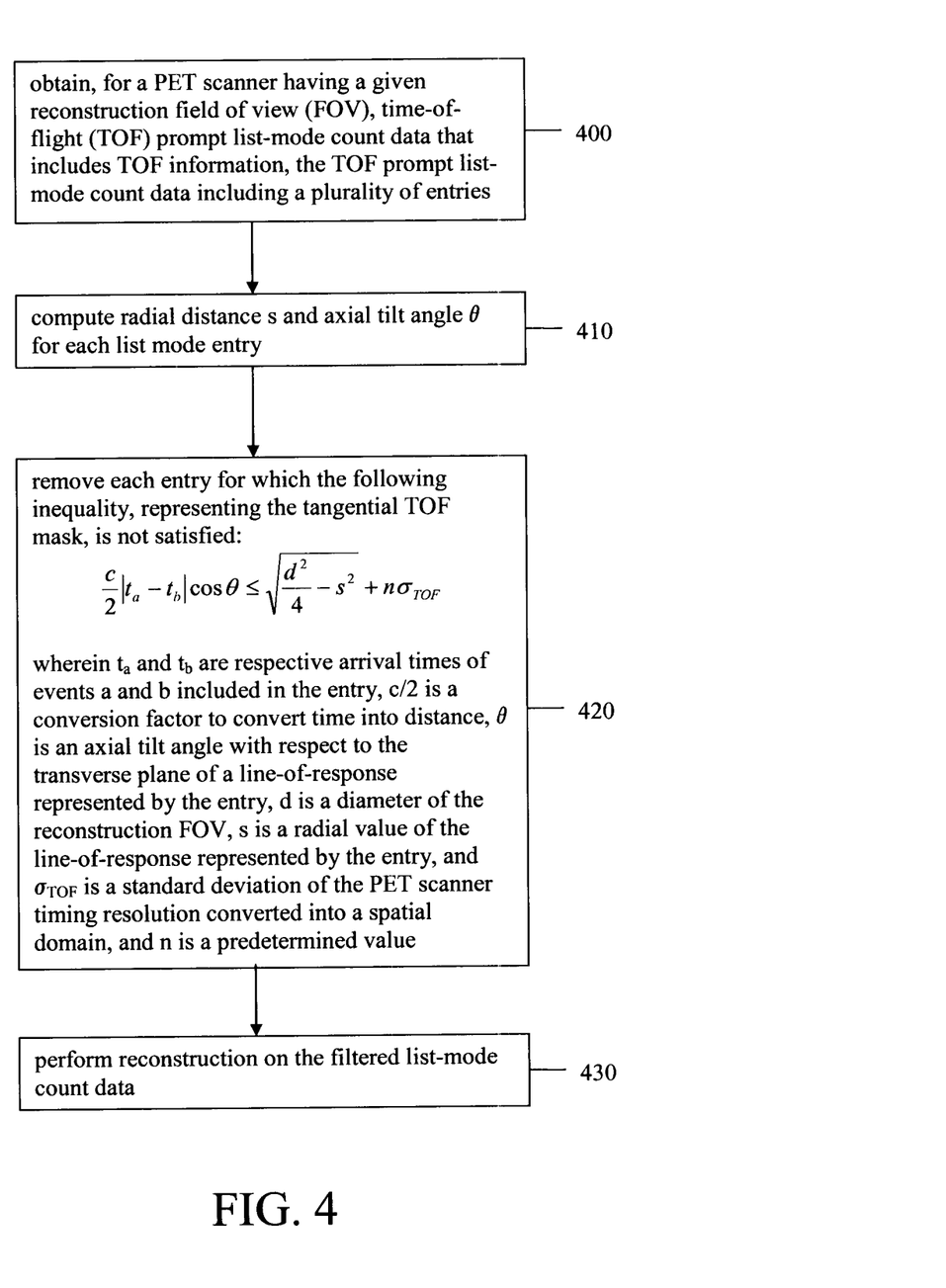
FIG. 4 is a flowchart of a method of filtering random events in PET according to one embodiment.

FIG. 3 illustrates an ellipse-shaped transverse-FOV with uniform distribution in the axial direction, i.e., an ellipse-shaped cylinder in 3D. The shaded area is the TOF mask for the ellipse FOV for a LOR with transverse rotation angle φ with respect to the x axis. The mask is generated by stretching the ellipse along ±t dimension by $3\sigma_{TOF}$. Note that for a non-circular reconstruction FOV, such as an ellipse, the shape of the TOF-mask depends on the LOR's transverse angle φ. FIG. 4 is a flowchart illustrating a method according to the present embodiments.

In step 400, for a PET scanner having a given reconstruction field of view (FOV), time-of-flight (TOF) prompt (or delay) list-mode count data that includes TOF information is obtained, the TOF prompt (or delay) list-mode count data including a plurality of entries.

Non-TOF list mode data generally has the following format for each coincident event: $\{x_a, z_a, x_b, z_b, e_a, e_b\}$ wherein $x_a$, $x_b$ are the incident transverse crystal numbers of events a and b, respectively; $z_a$, $z_b$ are the incident axial crystal numbers of events a and b, respectively; and $e_a$, $e_b$ are the energy levels of events a and b, respectively. Similarly, TOF list mode data has the format $\{x_a, z_a, x_b, z_b, e_a, e_b, tof\}$, wherein tof is the arrival time difference of events a and b, i.e., $tof = t_a - t_b$.

Note that a delayed coincidence window method can be used to generate TOF delay list-mode data, which can also be used in the random event filtering methods disclosed herein. Thus, in step 400, delay list-mode data can be obtained.

In step 410, the radial distance s and the axial tilt angle θ is calculated for each entry in the list-mode data.

In step 420, the obtained prompt list-mode count data is filtered by removing those entries in the obtained prompt list-mode count data that represent emission points lying outside a tangential TOF mask (e.g., the mask shown in FIG. 2) to obtain filtered list-mode count data.

In particular, the filtering is performed by removing each entry for which the following inequality, representing the tangential TOF mask, is not satisfied:

$$\frac{c}{2}|t_a - t_b|\cos\theta \le \sqrt{\frac{d^2}{4} - s^2} + n\sigma_{TOF}$$

wherein $t_a$ and $t_b$ are respective arrival times of events a and b included in the entry, c/2 is a conversion factor to convert time into distance, θ is an axial tilt angle with respect to the transverse plane of a line-of-response represented by the entry, d is a diameter of the reconstruction FOV, s is a radial value of the line-of-response represented by the entry, $\sigma_{TOF}$ is a standard deviation of the PET scanner timing resolution converted into a spatial domain, and n is a predetermined value that is preferable in the range of [2,3].

In step 430, PET image reconstruction is performed on the filtered list-mode count data.

Figure 5:
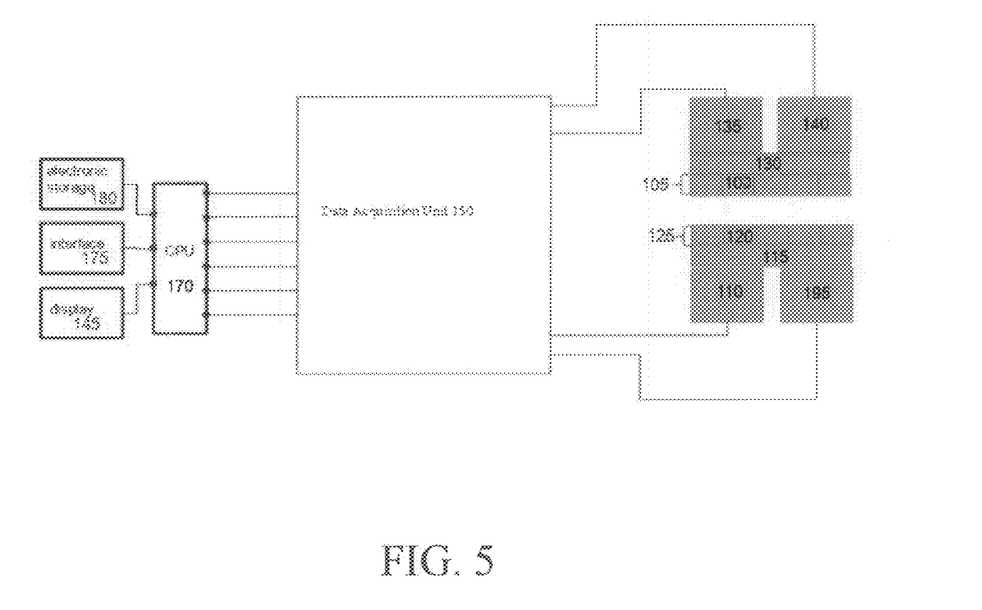
FIG. 5 illustrates PET system hardware according to one embodiment.

FIG. 5 shows an exemplary PET hardware configuration that can be used with the present embodiments. In FIG. 5, photomultiplier tubes 135 and 140 are arranged over light guide 130, and the array of scintillation crystals 105 is arranged beneath the light guide 130. A second array of scintillation crystals 125 is disposed opposite the scintillation crystals 105 with light guide 115 and photomultiplier tubes 195 and 110 arranged thereover.

In FIG. 5, when gamma rays are emitted from a body under test, the gamma rays travel in opposite directions, approximately 180° from each other. Gamma ray detection occurs simultaneously at scintillation crystals 100 and 120, and a scintillation event is determined when the gamma rays are detected at scintillation crystals 100 and 120 within a predefined time limit. Thus, the gamma ray timing detection system detects gamma rays simultaneously at scintillation crystals 100 and 120. However, for simplicity only, gamma ray detection is described relative to scintillation crystal 100. One of ordinary skill in the art will recognize, however, that the description given herein with respect to scintillation crystal 100 is equally applicable to gamma ray detection at scintillation crystal 120.

Each photomultiplier tube 110, 135, 140 and 195 is respectively connected to data acquisition unit 150. The data acquisition unit 150 includes hardware configured to process the signals from the photomultiplier tubes. The data acquisition unit 150 measures the arrival time of the gamma ray. The data acquisition unit 150 produces two outputs (one for the combination of PMT 135/140 and one for the combination of PMT 110/195) which encodes the time of the discriminator pulse relative to a system clock (not shown). For a time-of-flight PET system, the data acquisition unit 150 typically produces a time stamp with an accuracy of 15 to 25 ps. The data acquisition unit measures the amplitude of the signal on each PMT (four of the outputs from data acquisition unit 150).

The data acquisition unit outputs are provided to a CPU 170 for processing. The processing consists of estimating an energy and position from the data acquisition unit outputs and an arrival time from the time stamps output for each event, and may include the application of many correction steps, based on prior calibrations, to improve the accuracy of the energy, position, and time estimates.

Moreover, the CPU 170 is configured to perform a method for estimating random events according to the flowchart shown in FIG. 4 and described above.

As one of ordinary skill in the art would recognize, the CPU 170 can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog or any other hardware description language and the code may be stored in an electronic memory directly within the FPGA or CPLD, or as a separate electronic memory. Further, the electronic memory may be non-volatile, such as ROM, EPROM, EEPROM or FLASH memory. The electronic memory may also be volatile, such as static or dynamic RAM, and a processor, such as a microcontroller or microprocessor, may be provided to manage the electronic memory as well as the interaction between the FPGA or CPLD and the electronic memory.

Alternatively, the CPU 170 may be implemented as a set of computer-readable instructions stored in any of the above-described electronic memories and/or a hard disc drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art.

Once processed by the CPU 170, the processed signals are stored in electronic storage 180, and/or displayed on display 145. As one of ordinary skill in the art would recognize, electronic storage 180 may be a hard disk drive, CD-ROM drive, DVD drive, FLASH drive, RAM, ROM or any other electronic storage known in the art. Display 145 may be implemented as an LCD display, CRT display, plasma display, OLED, LED or any other display known in the art. As such, the descriptions of the electronic storage 180 and the display 145 provided herein are merely exemplary and in no way limit the scope of the present advancements.

FIG. 5 also includes an interface 175 through which the gamma ray detection system interfaces with other external devices and/or a user. For example, interface 175 may be a USB interface, PCMCIA interface, Ethernet interface or any other interface known in the art. Interface 175 may also be wired or wireless and may include a keyboard and/or mouse or other human interface devices known in the art for interacting with a user.

While certain embodiments have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method of reducing random events in positron emission tomography (PET) list mode data, the method comprising:
obtaining, for a PET scanner having a given reconstruction field of view (FOV), time-of-flight (TOF) prompt list-mode count data that includes TOF information, the TOF prompt list-mode count data including a plurality of entries;
filtering the obtained prompt list-mode count data by removing those entries in the obtained prompt list-mode count data that represent emission points lying outside a tangential TOF mask to obtain filtered list-mode count data; and
performing reconstruction on the filtered list-mode count data to generate a PET image.

2. The method of claim 1, wherein the filtering step comprises:
removing each entry for which the following inequality, representing the tangential TOF mask, is not satisfied:

$$\frac{c}{2}|t_a - t_b|\cos\theta \leq \sqrt{\frac{d^2}{4} - s^2} + n\sigma_{TOF}$$

wherein $t_a$ and $t_b$ are respective arrival times of events a and b included in the entry, c/2 is a conversion factor to convert time into distance, θ is an axial tilt angle with respect to the transverse plane of a line-of-response represented by the entry, d is a diameter of the reconstruction FOV, s is a radial value of the line-of-response represented by the entry, $\sigma_{TOF}$ is a standard deviation of the PET scanner timing resolution converted into a spatial domain, and n is a predetermined value.

3. The method of claim 1, further comprising determining the tangential TOF mask based on a standard deviation of the PET scanner timing resolution.

4. A method of reducing random events in positron emission tomography (PET) list mode data, the method comprising:
obtaining, for a PET scanner having a given reconstruction field of view (FOV), time-of-flight (TOF) delay list-mode count data that includes TOF information, the TOF delay list-mode count data including a plurality of entries;
filtering the obtained delay list-mode count data by removing those entries in the obtained delay list-mode count data that represent emission points lying outside a tangential TOF mask to obtain filtered list mode count data; and
performing reconstruction on the filtered list-mode count data to generate a PET image.

5. The method of claim 4, further comprising determining the tangential TOF mask based on a standard deviation of the PET scanner timing resolution.

6. An apparatus for reducing random events in positron emission tomography (PET) list mode data, the apparatus comprising:
a memory storing, for a PET scanner having a given reconstruction field of view (FOV), time-of-flight (TOF) prompt list-mode count data that includes TOF information, the TOF prompt list-mode count data including a plurality of entries; and
a processor configured to filter the obtained prompt list-mode count data by removing those entries in the obtained prompt list-mode count data that represent emission points lying outside a tangential TOF mask to obtain filtered list-mode count data, and perform reconstruction on the filtered list-mode count data to generate a PET image.

7. The apparatus of claim 6, wherein the processor is further configured to:
remove each entry for which the following inequality, representing the tangential TOF mask, is not satisfied:

$$\frac{c}{2}|t_a - t_b|\cos\theta \leq \sqrt{\frac{d^2}{4} - s^2} + n\sigma_{TOF}$$

wherein $t_a$ and $t_b$ are respective arrival times of events a and b included in the entry, c/2 is a conversion factor to convert time into distance, θ is an axial tilt angle with respect to the transverse plane of a line-of-response represented by the entry, d is a diameter of the reconstruction FOV, s is a radial value of the line-of-response represented by the entry, $\sigma_{TOF}$ is a standard deviation of the PET scanner timing resolution converted into a spatial domain, and n is a predetermined value.

8. The apparatus of claim 6, wherein the processor is further configured to determine the tangential TOF mask based on a standard deviation of the PET scanner timing resolution.

9. An apparatus for reducing random events in positron emission tomography (PET) list mode data, the apparatus comprising:
a memory storing, for a PET scanner having a given reconstruction field of view (FOV), time-of-flight (TOF) delay list-mode count data that includes TOF information, the TOF delay list-mode count data including a plurality of entries; and
a processor configured to filter the obtained delay list-mode count data by removing those entries in the obtained delay list-mode count data that represent emission points lying outside a tangential TOF mask to obtain filtered list-mode count data, and perform reconstruction on the filtered list-mode count data to generate a PET image.

10. The apparatus of claim 9, wherein the processor is further configured to determine the tangential TOF mask based on a standard deviation of the PET scanner timing resolution.

11. A non-transitory computer-readable medium storing a program that, when executed by a processor, causes the processor to perform a method, comprising:
- obtaining, for a PET scanner having a given reconstruction field of view (FOV), time-of-flight (TOF) prompt list-mode count data that includes TOF information, the TOF prompt list-mode count data including a plurality of entries;
- filtering the obtained prompt list-mode count data by removing those entries in the obtained prompt list-mode count data that represent emission points lying outside a tangential TOF mask to obtain filtered list-mode count data; and
- performing reconstruction on the filtered list-mode count data to generate a PET image.

12. The computer-readable medium of claim 11, wherein the method further comprises determining the tangential TOF mask based on a standard deviation of the PET scanner timing resolution.

* * * * *